(12) United States Patent
Park

(10) Patent No.: US 7,557,195 B2
(45) Date of Patent: Jul. 7, 2009

(54) STOICHIOMETRIC CONJUGATES OF BIOCOMPATIBLE POLYMERS AT THE UNPAIRED CYSTEINE RESIDUE OF THE WILD-TYPE G-CSF

(75) Inventor: Myung-Ok Park, Seoul (KR)

(73) Assignee: Biopolymed, Inc., Anam-dong, Seongbuk-gu, Seoul (KR)

( * ) Notice: Subject to any disclaimer, the term of this patent is extended or adjusted under 35 U.S.C. 154(b) by 369 days.

(21) Appl. No.: 10/508,721

(22) PCT Filed: Mar. 20, 2003

(86) PCT No.: PCT/KR03/00547

§ 371 (c)(1),
(2), (4) Date: Sep. 20, 2004

(87) PCT Pub. No.: WO03/078461

PCT Pub. Date: Sep. 25, 2003

(65) Prior Publication Data

US 2005/0143563 A1 Jun. 30, 2005

(30) Foreign Application Priority Data

Mar. 20, 2002 (KR) ...................... 10-2002-0015187

(51) Int. Cl.
*A61K 38/19* (2006.01)
*A61K 45/00* (2006.01)
*A61K 39/00* (2006.01)
*C08H 1/00* (2006.01)

(52) U.S. Cl. ................. 530/399; 424/85.1; 424/195.11; 424/198.1; 530/408

(58) Field of Classification Search ........................ None
See application file for complete search history.

(56) References Cited

U.S. PATENT DOCUMENTS

| | | | |
|---|---|---|---|
| 4,179,337 | A | 12/1979 | Davis |
| 4,301,144 | A | 11/1981 | Twashita |
| 4,810,643 | A | 3/1989 | Souza |
| 5,166,322 | A | 11/1992 | Shaw |
| 5,206,344 | A | 4/1993 | Katre |
| 5,643,575 | A | 7/1997 | Martinez |
| 5,766,897 | A | 6/1998 | Braxton |
| 5,919,455 | A | 7/1999 | Greenwald |
| 5,932,462 | A | 8/1999 | Harris |
| 5,951,974 | A | 9/1999 | Gilbert |

FOREIGN PATENT DOCUMENTS

| | | |
|---|---|---|
| AU | A-10948/92 | 8/1992 |
| EP | 0243153 | 10/1987 |
| EP | 0401384 | 3/1996 |
| EP | 0272703 | 10/1997 |
| EP | 0459630 | 8/1998 |
| EP | 0335423 | 3/2003 |
| EP | 0473268 | 10/2003 |
| WO | WO 8910932 | 11/1989 |
| WO | WO 9105798 | 5/1991 |
| WO | WO 94/00913 | 1/1994 |
| WO | WO 9511987 | 5/1995 |
| WO | WO 00/33881 | 6/2000 |
| WO | WO 01/87925 | 11/2001 |

OTHER PUBLICATIONS

Molineux et al, A new form of Filgrastim with sustained duration in vivo and enhanced ability to mobilize PBPC in both mice and humans, Exp. Hematol., 27, 1724-1734, 1999.*
Layton et al., Identification of a Functional Domain of Human Granulocyte Colony- stimulating Factor Using Neutralizing Monoclonal Antibodies, J.Biol. Chem., 266, 23815-23823, 1991.*
Abuchowski et al., Cancer therapy with chemically modified enzymes. I. Antitumor properties of polyethylene glycol-asparaginase conjugates.; Cancer Biochem. Biophys., 7, 175-186, 1984.
Algranati et al., A Branched Methoxy 40 KDA Polyethylene Glycol(PEG) Moiety Optimizes the Pharmacokinetics (PK) of Peginterferon a-2A(PEG-IFN) and may explain its enhanced efficacy In chronic Hepatitis C (CHC); Hepatology, 30 (suppl): 190A, (1999).
Davis et all, Hypouricaemic effect of polyethyleneglycol modified urate oxidase; Lancet, August:281-283, (1981).
Burgess, The nature and action of granulocyte-macrophage colony stimulating factors; A.W. and Metcalf, D, Blood, 56, 947-958, 1980.
The hematopoietic colony stimulating factors, Elservier, Amsterdam, 1984.
Nicola, N.A. et al., Purification of a factor inducing differentiation in murine myelomonocytic leukemia cells. Identification as granulocyte colony- stimulating factor; J. Biol. Chem., 258, 9017-9023, 1983.
Kinstler et al., Characterization and stability of N-terminally PEGylated rhG-CSF.; 1996, Pharmaceutical Res. 13(7): 996-1002.
Niven et al., Pulmonary absoption of polyethylene glycolated recombinant human granulocyte-colony stimulating factor (PEG rhG-CSF); J. of Contr., Rel. 32, 177-189, (1994).
Woghiren et al., Protected Thiol-Polyethylene Glycol: A New Activated Polymer for Reversible Protein Modification; Bioconjugate Chem 4:314 (1993).
Ishii et al., Effects of the state of the succinimido-ring on the fluorescence and structural properties of pyrene maleimide-labeled alpha alpha-tropomyosin.; Biophys J. 1986, 50:75-80).
Rich, D., et.al., Alkylating derivatives of amino acids and peptides. Synthesis of N-maleoylamino acids, [1-(N-maleoylglycyl)cysteinyl]oxytocin. Effects on vasopressin-stimulated water loss from isolated toad bladder.; J. Med. Chem. 18, 1004, 1975.
Welte et al. Purification and Biochemical Characterization of Human Pluripotent Hematopoietic Colony-Stimulating Factor; PNAS-USA 82: 1526-1530 (1985).
Souza et al. Recombinant human granulocyte colony-stimulating factor: effects on normal and leukemic myeloid cells; Science 232: 61-65 (1986).

(Continued)

Primary Examiner—Lorraine Spector
Assistant Examiner—Elly-Gerald Stoica

(57) ABSTRACT

The present invention relates to a conjugate of a biocompatible polymer and a G-CSF bonded through a thiol group of a dysteine residue in G-CSF at a 1:1 molar ratio, and methods of preparation thereof.

10 Claims, 8 Drawing Sheets

OTHER PUBLICATIONS

Gabrilove, Introduction and Overview of Hematopoietic Growth Factors; J. Seminars in Hematology, 26(2 Supp 2):1-4, (1989).

Jones et al. Bailliere's Clinical Hematology 2:183-111, 1989.

Nagata et al. The chromosomal gene structure and two mRNAs for human granulocyte colony-stimulating factor.; EMBO J 5: 575-581 (1986).

Moore et al. Synergy of Interleukin 1 and Granulocyte Colony-Stimulating Factor: In vivo Stimulation of Stem-Cell Recovery and Hematopoietic Regeneration Following 5-fluorouracil Treatment of Mice; PNAS-USA 84: 7134-7138, 1987.

Nagata et al,. Molecular cloning and expression of cDNA for human granulocyte colony-stimulating factor.; Nature, 319, 415 (1986).

Gurd FRN. Carboxymethylation. Method Enzymol 1972; B25: 424-49.

Pomroy N.C. et al., Solubilization of hydrophobic peptides by reversible cysteine PEGylation., Biochem. Biophys. Res. Commun., 1998 245:618-621.

Lee K.C. et al., Isolation, characterization and stability of positional isomers of mono-PEGylated salmon calcitonins., Pharm. Res., 1999 16:813-818.

Jensen-Pippo K.E. et al., Enteral bioavailability of human granulocyte colony stimulating factor conjugated with poly(ethylene glycol).; Pharm. Res. 1996 13:102-107.

Bowen S. et al., Relationship between molecular mass and duration of activity of polyethylene glycol conjugated granulocyte colony-stimulating factor nutein., Exp. Hematol., 1999 27:425-432.

Molineux et al., A new form of Filgrastim with sustained duration in vivo and enhan ed ability to mobilize PBPC in both mice and humans; Experimental Hematology 27:1724-1734 (1999).

Francesco M Veronese, Peptide and protein PEGylation: A review of problems and solutions.; Biomaterials22 (2001) 405-417.

Eun Kyung Yang, et al., Tissued Engineered Artificial Skin Composed of Dermis and Epidermis.; Artificial Organs 24(1): 7-17, 2000.

* cited by examiner

↙ : mono-PEG-G-CSF      ↙ : native-G-CSF

STOICHIOMETRIC CONJUGATES OF BIOCOMPATIBLE POLYMERS AT THE UNPAIRED CYSTEINE RESIDUE OF THE WILD-TYPE G-CSF

FIELD OF THE INVENTION

The present invention relates to conjugates with a 1:1 molar ratio of biocompatible polymer and G-CSF bonded through a thiol group of a cysteine residue in G-CSF and methods of preparation thereof.

BACKGROUND OF THE INVENTION

The present invention relates to G-CSF conjugates. The present invention also relates to a method of preparation of G-CSF conjugates with a 1:1 molar ratio between biocompatible polymer and G-CSF bonded through a thiol group of a cysteine residue in G-CSF by site-specific modification.

A variety of attempts have been made to increase the bioavailability of biologically active materials such as biologically active proteins or polypeptides, and/or extend the in vivo half-life of biologically active materials by linking them with biocompatible polymers. Conjugation of biologically active materials to biocompatible polymers may afford great advantages when they are applied in vivo and in vitro. When being covalently bonded to biocompatible polymers, biologically active materials may exhibit modified surface properties and solubility, and thus may be increased in solubility within water or organic solvents. Further, the presence of biocompatible polymers may make the proteins and/or polypeptides conjugated to them more stable, increase biocompatibility of the proteins and reduce immune response in vivo, as well as reduce the clearance rate of the proteins by the intestine, the kidney, the spleen, and/or the liver.

The most common conjugation method for reacting the proteins or polypeptides with biocompatible polymers such as PEG is achieved by reacting activated PEG to amino residues, such as lysine residues and N-termini, of proteins or peptides.

At this time, one of the hydroxyl groups of PEG is substituted with a methyl ether group while the other hydroxyl group is bonded to an electrophilic functional group to activate PEG. These methods are well known in many patents and publications.

U.S. Pat. No. 4,179,337 discloses a biologically active, substantially non-immunogenic water-soluble polypeptide composition comprising a biologically active polypeptide coupled with a coupling agent to at least one substantially linear polymer having a molecular weight of between about 500 to about 20,000 daltons selected from the group consisting of polyethylene glycol (PEG) and polypropylene glycol (PPG) wherein the polymer is unsubstituted or substituted by alkoxy or alkyl groups, wherein said alkoxy or alkyl group consists of 5 or fewer carbon atoms.

According to above-mentioned US patent, the polypeptide composition is prepared by reacting terminal carbon atoms bearing hydroxyl groups with PEG or PPG by using a coupling agent to provide an activated polymer containing a reactive terminal group, and coupling said reactive terminal group of the activated polymer to an amine group, lysine group or N-terminal group of a biologically active proteins or polypeptides. Thusly bonded PEG or PPG serves to prevent the activity of the polypeptide from being reduced.

However, this method resulted in conjugation of many PEGs to each of proteins or polypeptides, and thus, the biological activity of proteins or polypeptides was decreased. Therefore, the conjugates required purification by Reverse Phase Chromatography to obtain conjugates in which the proper number of PEGs were attached to each of proteins or polypeptides.

U.S. Pat. No. 4,301,144 discloses the hemoglobin modified by conjugating hemoglobin with polyalkylene glycol or its derivatives. It is described therein that modified hemoglobin is increased in retention time in the body, while retaining nearly the same oxygen carrying potential as native hemoglobin.

Various proteins are reported to show extended half-lives and reduced immunogenicity in plasma when being conjugated with PEG (Abuchowski et al., Cancer Biochem. Biophys., 7, 175-186, 1984).

U.S. Pat. No. 5,951,974 and Algranati et al (Hepatology, 40 (suppl), 190A, 1999) describe that PEGylation of alpha interferon with PEG12000 as well as branched PEG40000 decreases the clearance rate of alpha interferon, to enable once-weekly subcutaneous injection, instead of 3 times a week injection for native interferon.

Davis et al (Lancet, 2, 281-283, 1981) demonstrated that uricase-PEG conjugates showed increased in vivo half-life and showed reduced side effects during the metabolism of uric acid.

Colony Stimulating Factor (CSF), an acidic glycoprotein, is an important factor for survival, proliferation, differentiation of Hematopoietic Progenitor Cells (Burgess, A. W. and Metcalf, D, Blood, 56, 947-958, 1980, The hematopoietic colony stimulating factors, Elservier, Amsterdam, 1984). G-CSF has been known as a factor stimulating differentiation and proliferation of bone marrow precursor cells to granulocytes (Nicola, N. A., Metcalf, D., Matsumoto, M. and Johnson, G. R., J. Biol. Chem., 258, 9017-9023, 1983). Since mass production of CSF, which stimulates and control the proliferation and differentiation of the white blood cells, neutrophils and macrophages, has been achieved possible by using recombinant DNA technology, it is recognized that therapeutic use of G-CSF will be effective to prevent myelosuppression or enhance the recovery of bone marrow after treatment with anticancer agents. Therefore, many attempts have been made to obtain the several benefits achievable by using biocompatible polymers such as PEG to modify G-CSF.

For example, G-CSF can be reacted with methoxy PEG carboxymethyl-N-hydroxy succinimidyl ester to produce the modified G-CSF-polymer conjugates and the unstable linker of the product has been removed by treatment with 2 moles of hydroxylamine (pH7.3) followed by decreasing the pH to 3.5 (Kinstler et al., 1996, *Pharmaceutical Res.* 13(7): 996-1002).

Also, Niven et al (J. of Contr., Rel. 32, 177-189, 1994) demonstrated PEG conjugation of recombinant human granulocyte-colony stimulating factor (hereinafter, referred to as rhG-CSF) showed a more intense and extended white blood cell response relative to rhG-CSF alone. EP 0,401,384 describes the methods and materials to conjugate PEG to G-CSF and EP 0,473,268 describes the G-CSF conjugates between G-CSF analogs and water-soluble polymer, or PEG, via covalent bonding.

However, the biological activity of proteins has been reduced by conjugation of proteins and polymers through amine groups of proteins as described above. It is also problematic in terms of producing heterogeneous mixtures having a few PEGs attached to different numbers or sites of proteins. Therefore, an additional purification process is necessary to obtain PEG-protein conjugates having the same number of PEGs attached, the same attachment site, or homogeneous PEG-protein conjugates, and thus, this results in very low yield of final products.

The alternative to these problems is to conjugate biocompatible polymers to certain residues such as His, Trp, Asp, Glu of proteins or polypeptides, while retaining the biological activity of proteins or polypeptides. However, these residues are not suitable for conjugation with polymers since they are generally located in or near the active sites, or not exposed at the surface of proteins. Also, the numbers of these residues in proteins are too low to be conjugated with sufficient numbers of polymers to extend the plasma half-life of proteins significantly, and the reaction condition is not site-specific, as well as the reaction condition for site-specific conjugation being too harsh, thus decreasing the biological activity of proteins.

The site-specific modification of proteins with polymers through a thiol group of a cysteine residue is the one method to overcome this problem. In general, only a few proteins possess the accessible thiol group(s) and several methods of site-specific conjugation have been suggested to conjugate PEGs to natural thiol groups of cysteines or substituted cysteines by genetic engineering method.

For example, in order to conjugate PEG to thiol groups of cysteines in proteins or polypeptides, it is known that a stable symmetric disulfide is obtained by using PEG-ortho-pyridyl-disulfide (Woghiren et al. *Bioconjugate Chem* 1993, 50:75-80), and an activated double bond is reacted with thiol groups by the Michael reaction using PEG-maleimide. (Ishii et al., *Biophys J.* 1986, 50:75-80). Also, Shaw et al. (U.S. Pat. No. 5,166,322) describes the preparation of PEG-IL-3 by reacting the activated PEG, or sulfo-succinimidyl 4-(N-maleimidomethyl)cyclohexane-1-carboxylate activated PEG with the thiol groups of cysteine residues substituted for a lysine residue.

Also, Katre et al. (U.S. Pat. No. 5,206,344) describes the conjugation of an IL-2 mutant having a substituted cysteine at a certain site of IL-2, with activated PEG, or maleimido-6-amidocaproyl ester activated PEG4000. Rich et al. (Rich, D., et. al., *J. Med. Chem.* 18, 1004, 1975) reported the chemical modification of thiol groups of proteins using gamma-maleimido butyric acid and beta-maleimido propionic acid.

Braxton et al. (U.S. Pat. No. 5,766,897) describes PEG-cysteine protein conjugates, and especially the detailed method for covalent conjugation of cysteine groups of protease Nexin-1 with mPEG-maleimide.

WO 01/87925 describes a method of obtaining refolded soluble proteins having at least one free cysteine residue from insoluble or aggregated proteins, and exemplifies cysteine-reactive PEGs and PEGylated proteins, for example PEGylated G-CSF formed from cysteine-reactive PEG as examples of reactive cysteine residues. However, in relation with cysteine-PEGylation of wild type G-CSF, the PCT publication states clearly that wild type G-CSF was not PEGylated under the reaction conditions of this publication, as specifically described in Example 10.

These methods mentioned previously relate to methods for conjugating biocompatible polymers to thiol groups of cysteine residues of proteins or polypeptides, or relate to methods for increasing the biological activity of proteins conjugated with a number of biocompatible polymers. However, these works have not reported that 1:1 conjugates between a biocompatible polymer and a thiol group of a cysteine residue of G-CSF unexpectedly showed the significantly improved effect, for example, improved stability and biological activity.

Although G-CSF contains 5 cysteine residues, the present inventors found that G-CSF was bound to a biocompatible polymer stoichiometrically at a 1:1 molar ratio under generally known reaction condition through a thiol group of a cysteine residue and these conjugates had more improved stability and biological activity compared to G-CSF conjugates with several PEGs attached.

The G-CSF conjugates of the present invention are obtained as protein-polymer conjugates at a 1:1 molar ratio and thus provide a homogeneous product which may have benefits in the aspect of clinical study and better stability profiles than the conjugates bonded through amine groups of G-CSF. Therefore, G-CSF conjugates of the present invention have an additional advantage that a further purification process using the preparative column is not necessary.

SUMMARY OF THE INVENTION

The present invention provides biocompatible polymer-G-CSF conjugates with 1:1 molar ratio and methods for preparation thereof.

These conjugates provide more improved stability and biological activity compared to G-CSF conjugates with several PEGs attached.

The G-CSF conjugates of the present invention provide a homogeneous product and a further purification process using the preparative column is not necessary.

DETAILED DESCRIPTION OF THE INVENTION

Figure 1:
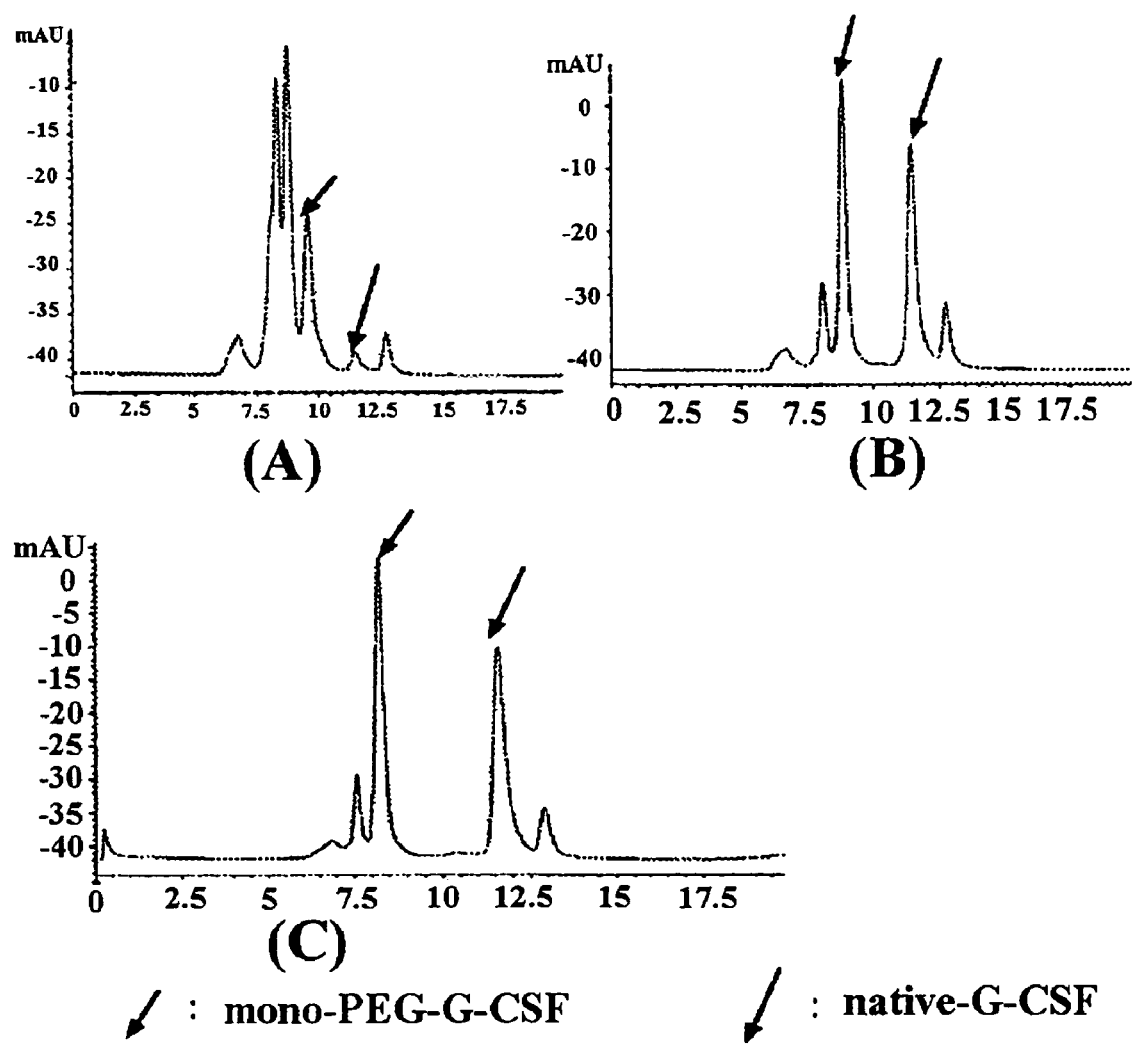
FIG. 1 shows the size exclusion chromatography result of mPEG5000-NHS-G-CSF(A), mPEG10000-NHS-G-CSF(B) and mPEG20000-NHS-G-CSF(C) formed by reaction of mPEG5000-NHS(A), mPEG10000-NHS(B), and mPEG20000-NHS(C) with G-CSF.

The present invention relates to the conjugates of biocompatible polymer and G-CSF bonded through a thiol group of a cysteine residue in G-CSF at a 1:1 molar ratio and methods of preparation thereof.

G-CSF

G-CSF, granulocyte colony stimulating factor, of the present invention is an important factor regulating proliferation and differentiation of hematopoietic progenitor cells (Welte et al. PNAS-USA 82: 1526-1530 (1985); Souza et al. *Science* 232: 61-65 (1986) and Gabrilove, J. Seminars in Hematology 26:2 1-14, 1989). In addition, G-CSF stimulates the release of mature neutrophils from bone marrow and activates their fintional states. Intracellular human G-CSF is found in the plasma (Jones et al. *Bailliere's Clinical Hematology* 2:1 83-111, 1989). In general, human G-CSF is produced by fibroblasts, macrophages, T cell trophoblasts, endothelial cells and epithelial cells, and is the expressed product of a single copy gene consisting of 4 exons and 5 introns in chromosome 17. It was shown that alternative splicing produced two different cDNAs that encode polypeptides of 177 amino acids and 174 amino acids (Nagata et al. EMBO J. 5: 575-581 (1986)). The Polypeptide consisting of 174 amino acids was found to possess the most characteristic biological activity. G-CSF has interspecies cross-reactivity, in other words, when G-CSF is administered to mouse, canine or other mammal such as monkey, the continuous increase of neutrophils is detected (Moore et al. PNAS-USA 84: 7134-7138, 1987). Nakata et al. reported that a human squamous carcinoma cell line (CHU-II) from human oral cavity tumor constitutively produces large quantities of G-CSF.

They isolated several clones containing G-CSF complementary DNA from the cDNA library prepared with messenger RNA from CHU-II cells. The complete nucleotide sequences of two of these cDNAs were determined and the expression of the cDNA in monkey COS cells yielded a protein showing authentic G-CSF activity (Nagata et al,. *Nature,* 319, 415 (1986)). Also, Sauza et al isolated cDNA of G-CSF from human bladder carcinoma cell 5637, determined the complete nucleotide sequences thereof and expressed it in *E. coli* (Souza et al., Science 232, 61 (1986)).

In general, G-CSF which can be used in the present invention is preferably wild type G-CSF. Also, G-CSF which has the same amino acid sequence with wild type can be preferably used. G-CSF of the present invention is the form isolated from mammalian animals, the product of organic synthesis, or the expressed product of host cell or nucleotide DNA sequences obtained by genomic and cDNA cloning or recombinant DNA. Suitable host cells include various bacteria such as *E. coli*, yeast such as *S. cerevisiae*, and mammalian cells such as CHO cells and monkey cells. Depending on host cells used, the expressed product of G-CSF is produced in glycosylated form with mammalian or other eukaryotic carbohydrates, or in non-glycosylated form. Also, the expressed product of G-CSF includes a methionine residue at position 1. The present invention includes all kinds of G-CSF, although recombinant G-CSF, especially from *E. coli*, is economically preferable.

It has been reported that certain G-CSF variants show biological activity. For example. G-CSF variants are described in U.S. Pat. No. 4,810,643. Other examples are described in AU-A-76380/91, EP 0,459,630, EP 0,272,703, EP 0,473,268, EP 0,335,423, AU-A-10948/92, PCT US 94/00913 and EP 0,243,153, although the activities of each variant are not described. G-CSF and their variants can be obtained from the various sources and purified for use. For example, natural human G-CSF is separated from the human carcinoma cell line culture. Also non-human G-CSF from recombinant mouse, bovine, or dog can be also used. (WO 9,105,798 and WO 8,910,932). Preferably, G-CSF of the present invention is a G-CSF having the same number of cysteine residues as wild type G-CSF.

Biocompatible Polymers to Conjugate to G-CSF

The most preferable polymer of the present invention is PEG. In general, PEG is a hydrophilic polymer and known as polyethylene oxide, and its chemical conjugation with molecules or surfaces is commonly performed. The common structure of PEG is that of a linear molecule having hydroxyl groups at both ends and expressed as follows: HO—$CH_2CH_2$O—($CH_2CH_2$O)n-$CH_2CH_2$—OH, or HO-PEG-OH.

Biocompatible polymers of the present invention are intended to include not only linear polymers but also polymers as follows. Biocompatible polymers of the present invention include soluble, non-antigenic polymers linked to an activated functional group that is capable of being nucleophilically substituted through an aliphatic linker residue (U.S. Pat. Nos. 5,643,575 and 5,919,455). Biocompatible polymers of the present invention also include multi-armed, monofunctional and hydrolytically stable polymers, having two linker fragments which have polymer arms in central carbon atom, a residue which is capable of being activated for attachment to biologically active materials such as proteins, and side chains which can be hydrogen or methyl group, or other linker fragment (U.S. Pat. No. 5,932,462). In addition, biocompatible polymers of the present invention also include polymers of branched PEG in which the functional groups such as PEGs are attached to biologically active materials via linker arms having reporter residues (WO 00/33881).

Also, biocompatible polymers of the present invention include biocompatible polymers having the structural formula PEI-P-A, wherein PEI is ethyleneimine, P is a biocompatible polymer and A is a reactive functional group or methoxy (Korean patent application No. 10-2001-0074728). In this Korean patent application, the reactive functional group (A) includes (I) functional groups able to react with amino group, for example, carbonate (for example, p-nitrophenyl or succinimidyl), carbonyl imidazole, azlactone, cyclic imide thione and isocyanate or isothiocyanate; (II) functional groups able to react with carboxylic acid and reactive carbonyl group, for example, primary amine, or hydrazine and hydrazide functional group (such as acyl hydrazide, carbazate, semicarbazate, thiocarbazate etc.); (III) functional groups able to react with mercapto or sulfhydryl group, for example phenyl glyoxal; (IV) functional groups able to react with hydroxyl group, for example carboxylic acid; and (V) other nucleophiles able to react with electrophilic centers.

Also, biocompatible polymers of the present invention include activated biocompatible polymers with a peptide spacer having structural formula [P—$OCH_2$CO—Y]$_n$-(L)$_s$-(Q)$_t$-(Y')$_k$-A, wherein P and Q are the same or different, and independently a biocompatible polymer, t is 0 or 1, Y and Y' are the same or different, and each is a peptide consisting of 2 to 18 amino acids in any combination, k is an integer of 0 or 1, L is an aliphatic linker residue or diaminocarboxylic acid, s is 0 or 1, A is a reactive functional group, and n is 1 or 2 (Korean patent application No. 10-2001-0067369). In this Korean patent application, the reactive functional group (A) includes (I) functional groups able to react with amino groups, for example, carbonate (for example, p-nitrophenyl or succinimidyl), carbonyl imidazole, azlactone, cyclic imide thione, or isocyanate or isothiocyanate; (II) functional groups able to react with carboxylic acid and reactive carbonyl groups, for example, primary amine, or hydrazine and hydrazide functional groups (such as acyl hydrazide, carbazate, semicarbazate, thiocarbazate etc.); (III) functional groups able to react with mercapto or sulfhydryl groups, for example phenyl glyoxal; and (IV) functional groups able to react with hydroxyl groups, for example (carboxylic) acid, for example hydroxyl, amino, carboxyl, thiol group, and active methylene etc.

Preferred biocompatible polymers of the present invention include, but are not limited to, polyethylene glycol (PEG) and derivatives thereof, polypropylene glycol (PPG), polyoxyethylene (POE), polytrimethylene glycol, polylactic acid and derivatives thereof, polyacrylic acid and derivatives thereof, polyamino acid, poly (L-lysine), polyurethane, polyphosphazene, polyalkylene oxide (PAO), polysaccharide, dextran, polyvinyl pyrrolidone, polyvinyl alcohol (PVA), polyacrylamide and similar non-antigenic polymers. The polymers of the present invention have a molecular weight of between about 300 and 100,000 daltons and preferably between about 2,000 and 40,000 daltons.

Functional Group of Biocompatible Polymer

The biocompatible polymer needs to be activated to react with G-CSF through a thiol group of a cysteine residue of G-CSF by activating its functional group. The functional group is the activated group or moiety for linking to the biologically active materials. To conjugate the biologically active molecules to biocompatible polymers, one of the end groups of biocompatible polymers is converted to a reactive functional group suitable for conjugation. This process is referred to as "activation" and the product is called an "activated" polymer. For instance, to conjugate poly(alkylene oxides) to biologically active materials, one of hydroxyl end groups of the polymer is converted to a reactive functional group such as carbonate and the product is called an activated poly(alkylene oxide).

A preferred reactive functional group of the present invention includes, but is not limited to, maleimide, acetamide, pentenoic amide, butenoic amide, isocyanate, isothiocyanate, cyanuric chloride, 1,4-benzoquinone, and disulfide.

Preferable Conjugates of the Present Invention and Preparation Method Thereof

The preferable biocompatible polymer-G-CSF conjugate of the present invention relates to the conjugates of PEG and G-CSF through a thiol group of a cysteine residue of G-CSF at a 1:1 molar ratio. The conjugate with such as 1:1 binding ratio retains the biological activity of G-CSF and increased stability in vivo.

Preparation of biocompatible polymer-G-CSF conjugates through a thiol group of G-CSF.

The conjugation of PEG with a protein through thiol groups of a protein can be performed by a general method.

For example, a thiol group can bind to an activated double bond of PEG-maleimide by the Michael reaction (Ishii et al., *Biophys J.* 1986, 50:75-80). Another example of such reaction can be performed by using PEG-iodoacetoamide, as is well known in protein chemistry. This method has an advantage of producing a stable PEG-cysteine derivative, carboxymethyl cysteine, which is readily analyzed by amino acid analysis (Gard FRN. Carboxymethylation. Method Enzymol 1972; B25: 424-49). other examples are as follows: the method to obtain stable symmetric disulfide bonds using PEG-ortho-pyridyl-disulfide (Woghiren et al. *Bioconjgate Chem* 1993, 50:75-80); the method to react activated PEG, sulfosuccinimidyl 4-(N-maleimidomethyl)cyclohexane-1-carboxylated PEG, with a thiol groups of cysteine residues to form covalent bonds (U.S. Pat. No. 5,166,322); the method to react activated PEG, maleimido-6-aminocaproyl ester PEG4000 with substituted cysteine residues of IL-2 mutant by a mutagenesis method (U.S. Pat. No. 5,206,344); the method to chemically alter thiol groups of proteins using gamma-maleimido butyric acid and beta-maleimido propionic acid (Rich et al., *J. med. Chem.* 18, 1004, 1975) etc.

The present invention has used a method of reacting activated polymers, mPEG-Gly-Gly-maleimide, mPEG-maleimide and mPEG-chloroacetamide, respectively, with G-CSF through a thiol group of a cysteine residue of G-CSF. Briefly, G-CSF was reacted with mPEG(5000 or 20000)-Gly-Gly-maleimide, mPEG(5000 or 20000)-malemide or mPEG(5000 or 12000)-chloroacetamide to produce conjugates of biologically active material, G-CSF and biocompatible polymers, i.e., MPEG(5000 or 20000)-Gly-Gly-maleimide-G-CSF, mPEG(5000 or 20000)-maleimide-G-CSF and MPEG(5000 or 12000)-Gly-Gly-acetamide-G-CSF.

As mentioned hereinbefore, G-CSF is a protein consisting of 174 or 177 amino acids, having 5 cysteine residues in which four of them form disulfide bonds and only one is free. In contrast to conventional method in which PEG was conjugated to proteins through amino groups of the proteins with the result that several PEGs were conjugated to one protein, when biocompatible PEG is conjugated to G-CSF through the a thiol group of a cysteine residue of G-CSF according to the present invention, conjugates of PEG and G-CSF at a 1:1 molar ratio were obtained, i.e., one molecule of PEGs was reacted with a thiol group of only a free cysteine residue to produce PEG-conjugated G-CSF at a 1:1 molar ratio.

In general, the pH of reaction buffer for protein/peptide conjugation is preferably between 6 and 10. The suitable temperature for the conjugation reaction is in the range of 0 to 60° C. and preferably in the range of 4 to 30° C. Also, the reaction time of 5 minutes to 10 hours is preferable in this preparation.

The present inventors found that when PEG was conjugated to cysteine of G-CSF, aggregates having no biological activity of PEG-G-CSF were immediately formed. Therefore, the present inventors confirmed that treatment with a small amount of SDS, tween20, tween80 detergent etc. is necessary to prevent the aggregates from being formed. In other words, the present inventors confirmed that if not treated with any of such detergents, active PEG-G-CSF conjugates could not be obtained. In addition, if treated with reducing agent DTT instead of a detergent, the aggregates remained and any PEG-G-CSF conjugate was also inactive.

Therefore, to prevent aggregation, the present inventors have kept PEG-G-CSF conjugates of the present invention in cold storage with a small amount, i.e., 0.001% to 1%, preferably 0.003 to 0.5%, and more preferably 0.005% to 0.1% of SDS detergent.

In addition, the present inventors confirmed that SDS can be removed from PEG-G-CSF conjugates treated with SDS solution by ultra-filtration using centricon-30 (Milipore, USA) before administration in vivo. The present inventors also confirmed that after monomeric PEG-G-CSF conjugates (not forming aggregates) were isolated via treatment with SDS, such conjugates can be administrated in vivo without adding further SDS solution.

The following examples further describe and demonstrate embodiments within the scope of the present invention. The examples are given solely for the purpose of illustration and are not to be construed as limitations of the present invention, as many variations thereof are possible without departing from the spirit and scope of the invention.

PREFERRED EMBODIMENT OF THE PRESENT INVENTION

1. Preparation of Activated PEG

EXAMPLE 1

Preparation of mPEG(5000)-Gly-Gly-Maleimide (FIG. 1)

2 g of mPEG-OH (0.4 mM) was dissolved in 150 ml of THF under nitrogen atmosphere and then a small amount of Na and 0.1 g of naphthalene were added to stir at room temperature for 3 hours. 0.12 g of Gly-Gly ethyl ester (0.8 mM) was then added dropwise to the mixture at room temperature and stirred for another 15 hours.

After completion of the reaction, the reaction mixture was crystallized by adding cold ether under ice bath. The product was filtered, washed with 300 ml of ether, and dried under vacuum.

The resulting product, 1.80 g of mPEG(5000)-OCH2COGly-GlyCOOH was obtained (yield: 90%).

0.5 g of thusly obtained mPEG(5000)-OCH2COGly-Gly-COOH (0.1 mM) was then dissolved in 15 ml of methylene chloride (hereinafter referred to as "MC"), and 0.034 g of N-hydroxyphthalimide (hereinafter referred to as "NHP") (0.3 mM) and 0.062 g of N,N'-dicyclohexyl carbodiimide (hereinafter referred to as "DCC") (0.3 mM) were added with stirring. The reaction proceeded for 24 hours with stirring and heating up to 30° C. after which the mixture was cooled to room temperature, followed by filtration using Celite and charcoal, and then dried.

The resulting product was crystallized by adding 50 ml of isopropyl alcohol (herein after referred to as "IPA") under ice bath, filtered, washed with 200 ml of ether, and dried under vacuum to afford 0.43 g (yield: 83%) of the title polymer as a white solid.

0.3 g of white solid, mPEG(5000)-OCH2COGly-GlyNHP was dissolved in 15 ml of MC and 0.036 g of ethylenediamine (0.6 mM, hereinafter referred to as ETD) was added with stirring. After 24 hrs, the product was filtered using Celite and charcoal, and then dried.

The resulting product was crystallized by adding 50 ml of IPA under ice bath, filtered, washed with ether, and dried under vacuum to afford 0.25 g (yield: 83%) of mPEG(5000)-OCH2COGly-Gly-NH—CH2—CH2—NH2 as a white solid. Then, 100 mg of mPEG(5000)-OCH2COGly-Gly-NH—CH2—CH2—NH2 (0.018 mM) was dissolved in 10 ml of chloroform and 5 mg of methoxycarbonylmaleimide (0.036 mM) was added.

The mixture was stirred at 25° C. for 2 hours and unreacted excess reagent was removed by purification on a Sephadex G-25 column (BioRad). The resulting product was crystallized by adding 20 ml of IPA under ice bath, filtered, washed with ether, and dried under vacuum to afford 75 mg of product.

EXAMPLE 2

Figure 2:
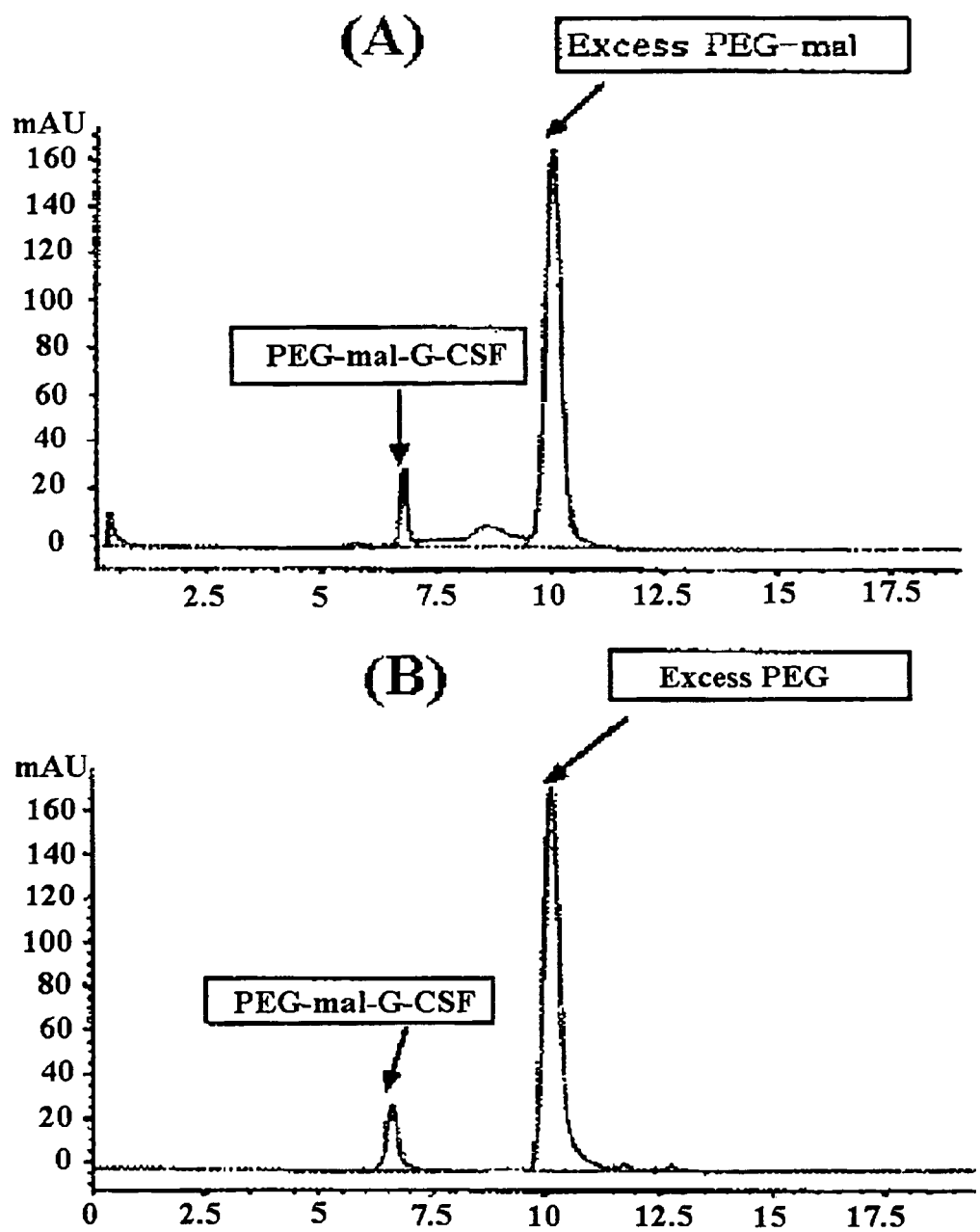
FIG. 2 shows the size exclusion chromatography result of mPEG5000-maleimide-G-CSF(A) and mPEG20000-maleimide-G-CSF(B) formed by reaction of 20 to 50-folds of mPEG5000-maleimide and mPEG20000-maleimide with G-CSF.

Preparation of mPEG(5000)-maleimide (FIG. 2)

1 g of mPEG(5000)-OH (0.2 mM) was dissolved in 100 ml of MC and 20 mg of 1,4-nitrophenylchloroformate(0.3 mM) and 5.3 mg of pyridine(0.24 mM) was added. After 4 hrs at 25° C. with stirring, 72 mg of ETD (0.6 mM) was added. The reaction proceeded for 24 hours with stirring and the mixture was filtered using Celite and charcoal, and then dried. The resulting product was crystallized by adding 50 ml of IPA under ice bath, filtered, washed with 500 ml of ether, and dried under vacuum to afford 0.85 g of mPEG(5000)-OCH2CO—NH—CH2—CH2—NH2 (yield: 83%) as a white solid.

Then, 50 mg of mPEG(5000)-OCH2CO—NH—CH2—CH2—NH2 (0.009 mM) was dissolved in 5 ml of chloroform, and 2.5 mg of methoxycarbonylmaleimide (0.018 mM) was added. The mixture was stirred at room temperature for 2 hours and unreacted excess reagent was removed by purification on Sephadex G-25 column (BioRad). The resulting product was crystallized by adding 50 ml of IPA under ice bath, filtered, washed with 200 ml of ether, and dried under vacuum to afford 38 mg of product.

EXAMPLE 3

Preparation of mPEG(2000)-Gly-Gly-maleimide 2 g of mPEG(20000)—OH (0.1 mM) was dissolved in 30 ml of THF under nitrogen atmosphere and then a small amount of Na and 0.1 g of naphthalene were added to stir at room temperature for 3 hours. 0.12 g of Gly-Gly ethyl ester (0.8 mM) was then added dropwise to the mixture at room temperature and stirred for another 15 hours. After completion of reactions, the reaction mixture was crystallized by adding cold ether under ice bath. The product was filtered, recovered, washed with ether, and dried under vacuum.

The resulting product, 1.80 g of mPEG(20000)—OCH2COGly-GlyCOOH was obtained (yield: 90%).

0.5 g of mPEG(20000)-OCH2COGly-GlyCOOH (0.1 mM) was then dissolved in 15 ml of MC, and 0.034 g of N—NHP (0.3 mM) and 0.062 g of N,N'-DCC (0.3 mM) was added. The reaction proceeded for 24 hours with stirring and heating to 30° C. and the mixture was cooled to room temperature followed by filtration using celite and charcoal, and then dried.

The resulting product was crystallized by adding 50 ml of IPA under ice bath, filtered, washed with ether, and dried under vacuum to afford 0.43 g (yield: 83%) of mPEG(20000)-OCH2COGly-GlyNHP as a white solid.

0.3 g of mPEG(20000)-OCH2COGly-GlyNHP was dissolved in 15 ml of MC with stirring and 0.036 g of ETD(0.6 mM) was added. After 24 hrs, the product was filtered using Celite and charcoal, and then dried.

The resulting product was crystallized by adding 50 ml of IPA under ice bath, filtered, washed with 100 ml of ether, and dried under vacuum to afford 0.25 g (yield: 83%) of tnPEG (20000)-OCH2COGly-Gly-NH—CH2—CH2—NH2.

Then, 100 mg of mPEG(20000)-OCH2COGly-Gly-NH—CH2—CH2—NH2 (0.018 mM) was dissolved in 10 ml of chloroform, and 5 mg of methoxycarbonylmaleimide (0.036 mM) was added. The mixture was stirred at 25° C. for 2 hours and unreacted excess reagent was removed on a Sephadex G-25 column (BioRad). The resulting product was crystallized by adding 30 ml of IPA under ice bath, filtered, washed with 200 ml of ether, and dried under vacuum to afford 75 mg of product as a white solid.

EXAMPLE 4

Preparation of mPEG(20000)-maleimide 1.4 g of mPEG(20000)-Gly-Gly-Maleimide (yield: 70%) was prepared using 2 g of mPEG(20000)-OH in the same manner as described in <Example 2>.

EXAMPLE 5

Preparation of mPEG(5000)-chloroacetamide 0.2 g of mPEG(5000)-amine (NOF, Japan) (0.04 mM) was dissolved in 5 ml of MC and 28.7 µl of chloroacetyl chloride (0.12 mM) was added at 25° C. followed up addition of 5.3 mg of pyridine (0.24 mM) with stirring for 48 hours. The reaction was terminated by addition 10 ml of water and the water layer was extracted three times using 20 ml of MC. The product was filtered and evaporated to obtain crude oil and crystalized by adding 50 ml of diethylether dropwise. The product was dissolved in 2 ml of MC and recrystallized in 300 ml of IPA:diethylether solution (1:4), filtered and dried under vacuum. The 180 mg of product was obtained as a white solid (yield 88%).

EXAMPLE 6

Preparation of mPEG(12000)-chloroacetamide 1.7 g of mPEG(12000)-chloroacetamide (yield: 85%) was synthesized using 2 g of mPEG (12000)-amine (NOF, Japan) in the same manner as described in <Example 5>.

2. Activated Biocompatible Polymer-G-CSF Conjugates

When all of PEG-G-CSF formed by a thiol group conjugation at a cysteine of G-CSF were prepared in the following Examples, the present inventors kept the PEG-G-CSF conjugates of the present invention in cold storage with a small amount, i.e., 0.001% to 1%, preferably 0.003 to 0.5%, and more preferably 0.005% to 0.1% of SDS detergent. Such SDS solution can be removed by ultra-filtration using centricon-30 (Milipore, USA) before administration in vivo.

EXAMPLE 7

Preparation of mPEG(5000)-Gly-Gly-maleimide-G-CSF 1 mg of G-CSF ($5.26 \times 10^{-5}$ mM, Leucostim, Dong-A Pharmaceutical Co., Korea) in 1 ml of 0.1 M sodium phosphate, pH 8.5 was reacted with mPEG(5000)-Gly-Gly-maleimide (13.15 mg, $2.6 \times 10^{-3}$ mM) prepared in <Example 1>. The reaction proceeded with stirring at room temperature for 1 hour. The unreacted excess PEG was removed by using centricon-10 (Amicon, USA).

EXAMPLE 8

Preparation of mPEG(20000)-Gly-Gly-maleimide-G-CSF 1 mg of G-CSF ($5.26 \times 10^{-5}$ mM) in 1 ml of 0.1 M sodium phosphate, pH 8.5 was reacted with mPEG(20000)Gly-Gly-maleimide (52.6 mg, $2.6 \times 10^{-3}$ mM) prepared in <Example 3>. The reaction proceeded with stirring at room termperature for 1 hour. The unreacted excess PEG was removed by using centricon-30 (Amicon. USA).

EXAMPLE 9

Preparation of mPEG(5000)-maleimide-G-CSF 1 mg of G-CSF ($5.26 \times 10^{-5}$ mM) in 1 ml of 0.1 M sodium phosphate, pH 8.5 was reacted with mPEG(5000)-maleimide (14.5 mg, $2.6 \times 10^{-3}$ mM) prepared in <Example 2>. The reaction proceeded with stirring at room temperature for 1 hour. The unreacted excess PEG was then removed by using centricon-10 (Amicon, USA).

EXAMPLE 10

Preparation of mPEG(20000)-maleimide-G-CSF 1 mg of G-CSF ($5.26 \times 10^{-5}$ mM) in 1 ml of 0.1 M sodium phosphate, pH 8.5 was reacted with mPEG(20000)-maleimide (52.6 mg, $2.6 \times 10^{-3}$ mM) prepared in <Example 4>. The reaction proceeded with stirring at room temperature for 1 hour. The unreacted excess PEG was then removed by using centricon-30 (Amicon, USA).

EXAMPLE 11

Preparation of mPEG(5000)-acetamide-G-CSF 1 mg of G-CSF ($5.26 \times 10^{-5}$ mM) in 1 ml of 0.1 M CAPS buffer solution, pH 10 was reacted with mPEG(5000)-chloroacetamide (25 mg, $5 \times 10^{-3}$ mM) prepared in <Example 5>. The reaction proceeded with stirring at room temperature for 1 hour. The unreacted excess PEG was then removed by using centricon-10 (Amicon, USA).

EXAMPLE 12

Preparation of mPEG(12000)-acetamide-G-CSF 1 mg of G-CSF ($5.26 \times 10^{-5}$ mM) in 1 ml of 0.1 M CAPS buffer solution, pH 10 was reacted with mPEG(12000)-chloroacetamide (63 mg, $5 \times 10^{-3}$ mM) prepared in <Example 6>. The reaction proceeded with stirring at room temperature for 1 hour. The unreacted excess PEG was then removed by using centricon-30 (Amicon, USA).

3. Characterization of mPEG Modified G-CSF on Amine Group and mPEG Modified G-CSF on Thiol Group In <Example 9> and <Example 10>, it was shown that only one PEG5000 or PEG20000 was bonded to G-CSF by SDS-PAGE (lanes 2 and 3 of FIG. 8) and size exclusion chromatography (FIG. 2), although a 20 or 50 fold excess of PEG was used, relative to G-CSF, whereas unreacted native G-CSF was not detected. A and B of FIG. 2 show results of size exclusion chromatography of mPEG5000-maleimide-G-CSF and PEG20000-maleimide-G-CSF, respectively.

However, three fractions, mono-, di-, and tri-PEG-G-CSF were produced in case of mPEG-NHS (FIG. 1, A) due to random reaction of PEG-NHS with G-CSF through amine groups of G-CSF.

As shown in FIG. 1, the use of high molecular weight PEG species such as mPEG10000-NHS(B) or mPEG20000-NHS (C) produces more mono-PEG-G-CSF relative to di- or tri-PEG-G-CSF. However, this reaction results in lower product yield since a lot of unreacted G-CSF was detected.

As described above, the number of PEGs attached to G-CSF through amine group modification depends on the molar ratio of PEG to G-CSF, whereas only one PEG is bonded covalently to G-CSF through thiol group modification, although a 20 to 50 fold molar excess of PEG was used relative to G-CSF.

mPEG(5000, 10000, 20000)-NHS-G-CSF for comparison were prepared as described in <Example 13> and <Example 14>.

EXAMPLE 13

Preparation of mPEG(5000)-N-HS-G-CSF(A of FIG. 1)

1 mg of G-CSF ($5.26 \times 10^{-5}$ mM) in 1 ml of 0.1 M sodium phosphate, pH 7.0 was reacted with 1.32 mg of mPEG(5000)-NHS ($2.6 \times 10^{-4}$ mM, Shearwater Polymers, USA). The reaction proceeded with stirring at room temperature for 30 minutes. The unreacted excess PEG was then removed by using centricon-10 (Amicon, USA).

EXAMPLE 14

Figure 5:
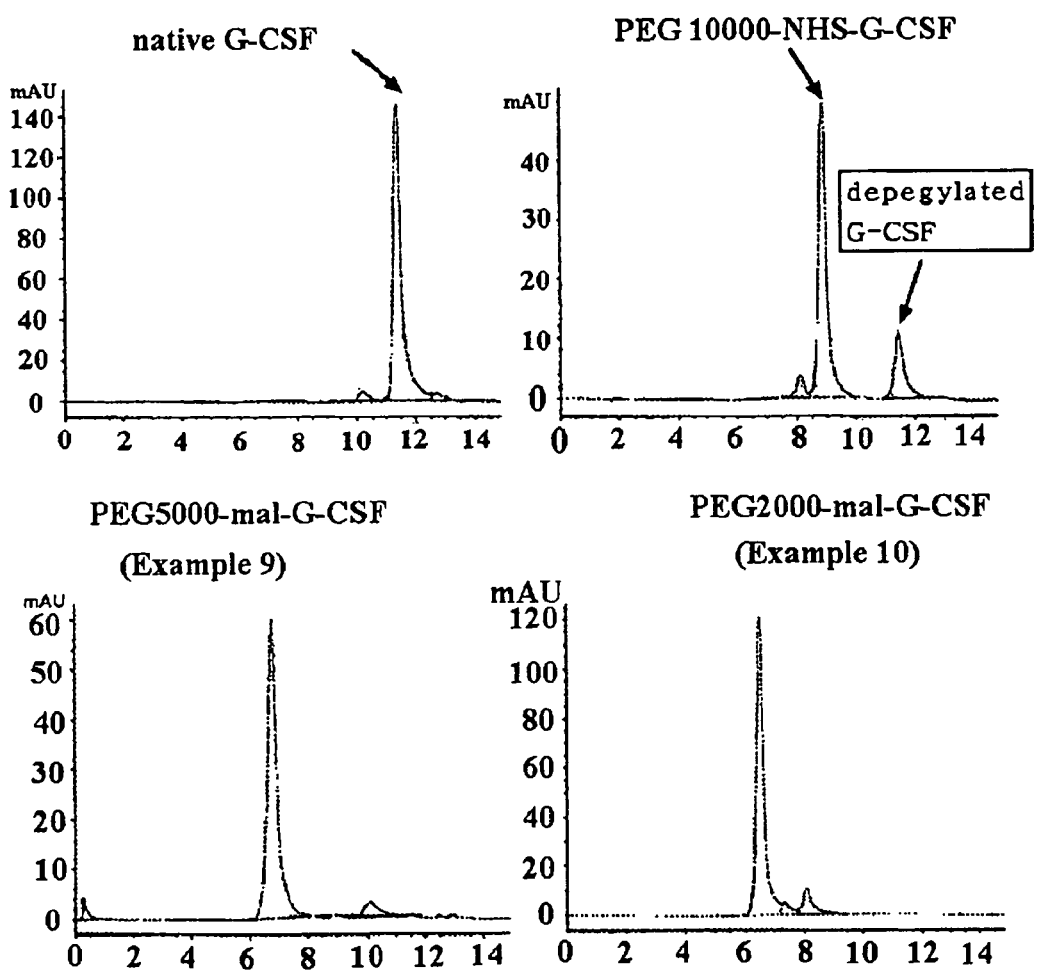
FIG. 5 shows the comparison of stabilities of mPEG10000-NHS-G-CSF, mPEG5000-maleimide-G-CSF and mPEG20000-maleimide-G-CSF by size exclusion chromatography.

Preparation of mPEG(10000)-NHS-G-CSF (B of FIG. 1 and FIG. 5)

1 mg of G-CSF ($5.26 \times 10^{-5}$ mM) in 1 ml of 0.1 M sodium phosphate, pH 7.0 was reacted with 5.26 mg of mPEG (10000)-NHS ($5.26 \times 10^{-4}$ mM, Shearwater Polymers, USA). The reaction proceeded with stirring at room temperature for 1 hour. The unreacted excess PEG was then removed by using centricon-30 (Amicon, USA).

EXAMPLE 15

Preparation of mPEG(20000)-NHS-G-CSF (C of FIG. 1)

1 mg of G-CSF ($5.26 \times 10^{-5}$ mM) in 1 ml of 0.1 M sodium phosphate, pH 7.0 was reacted with 5.6 mg of mPEG(10000)-NHS ($2.8 \times 10^{-4}$ mM, Shearwater Polymers, USA). The reaction proceeded with stirring at room temperature for 1 hour. The excess reagent was then removed by using centricon-30 (Amicon, USA).

4. Determination and Comparison of Biological Activity of PEG(5000, 20000)-maleimide-G-CSF and mPEG-NHS-G-CSF The number of PEG molecules attached to amine groups (N-terminal, lysine) of G-CSF increased with the molecular weight of PEG used, whereas the physiological activity was decreased. mPEG(20000)-NHS-G-CSF prepared as described in <Example 15> was separated into mono-mPEG (20000)-NHS-G-CSF and di-mPEG (20000)-NHS-G-CSF for comparison (FIG. 6).

EXAMPLE 16

Figure 6:
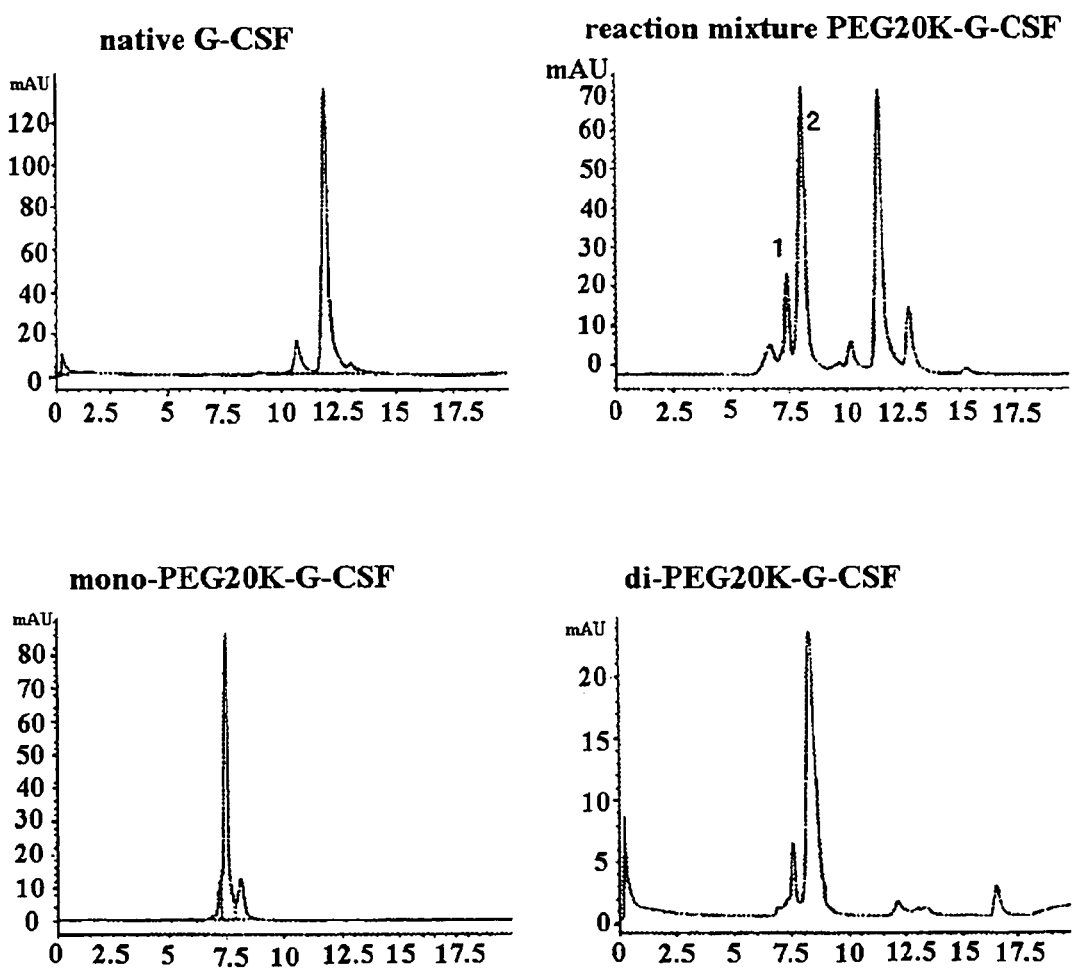
FIG. 6 shows the purified mono-mPEG(20000)-G-CSF and di-mPEG(20000)-G-CSF by HPLC.

Purification of mono-mPEG(20000)-NHS-G-CSF and di-mPEG(20000)-NHS-G-CSF (FIG. 6)

mPEG(20000)-NHS-G-CSF prepared in <Example 15> was separated by size-exclusion HPLC eluting with 0.1 M Phosphate buffer, pH 7.0 into mono- and di-mPEG(20000)-NHS-G-CSF. Each fraction was concentrated by using centricon-10 (Amicon, USA).

EXAMPLE 17

Comparison of Biological Activity

Figure 3:
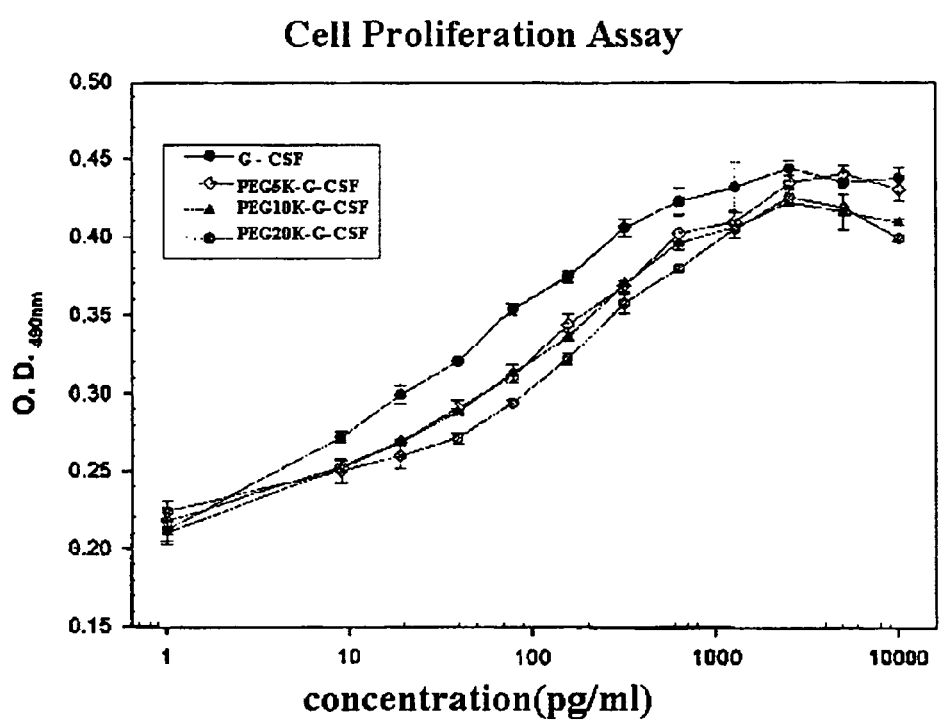
FIG. 3 shows the comparison of the biological activities of mPEG5000-NHS-G-CSF, mPEG10000-NHS-G-CSF and mPEG20000-NHS-G-CSF by cell proliferation assay.
Figure 4:
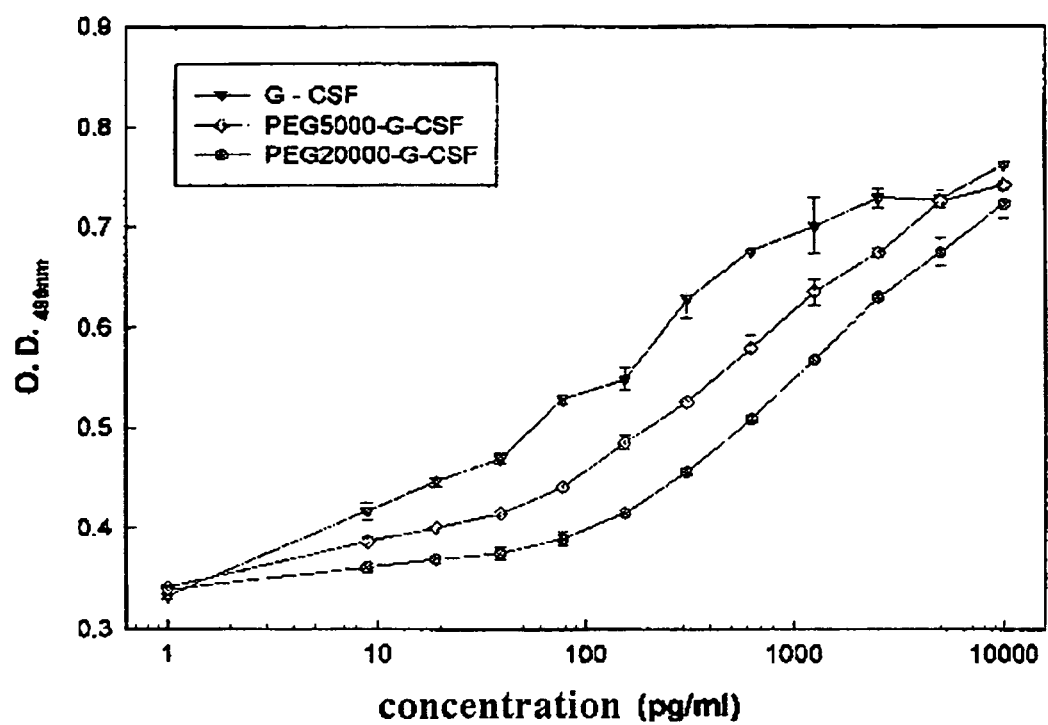
FIG. 4 shows the comparison of the biological activities of mPEG5000-maleimide-G-CSF and mPEG20000-maleimide-G-CSF by cell proliferation assay.

The activity of PEG-G-CSF was measured by Cell Proliferation Assay (CPE). The activity of PEG-NHS-G-CSF and PEG-Maleimide-G-CSF for the different molecular weights of PEG (PEG 5000, 10000 and 20000) with using native G-CSF as a control was determined, and the results are shown in FIG. 3 and FIG. 4, respectively. The figures show the biological activity decreased as the molecular weight of PEG increased.

The biological activities of native-G-CSF (control), mPEG-maleimide-G-CSF and mPEG-NHS-G-CSF (Examples 9 and 10, Examples 13 to 15) by CPE assay are shown in Table 1. mPEG(2000)-NHS-G-CSF conjugated at a lysine residue of G-CSF was separated by the same method as described in <Example 16> into mono- and di-mPEG20000-NHS-G-CSF.

Figure 7:
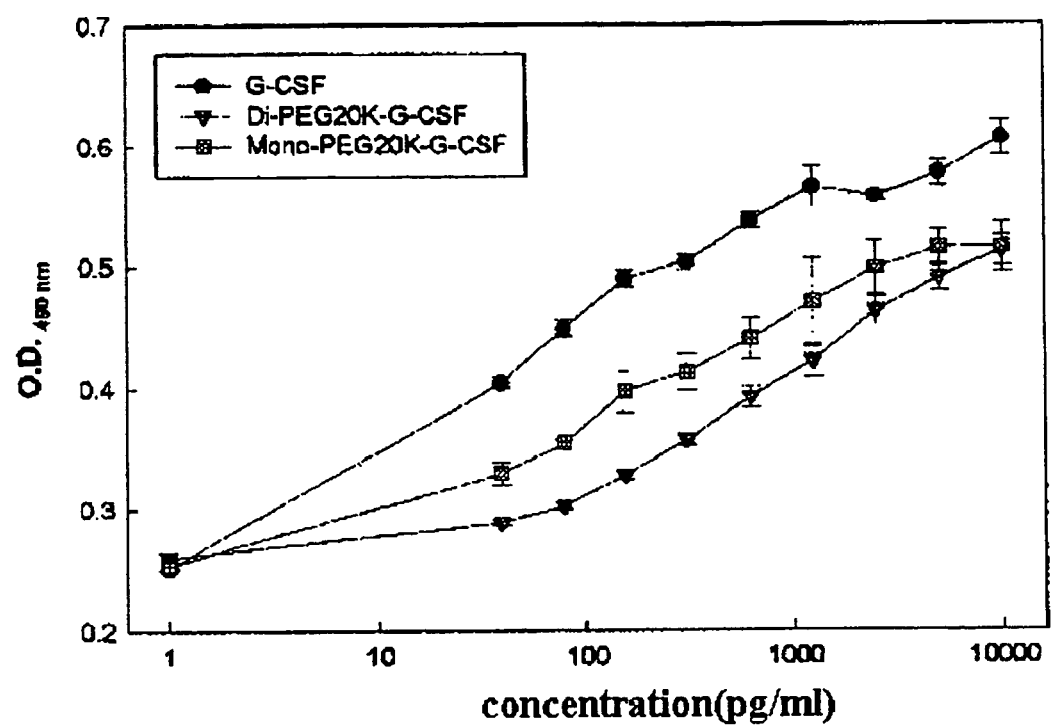
FIG. 7 shows the comparison of the biological activities of mono-mPEG(20000)-G-CSF and di-mPEG(20000)-G-CSF.

Also the activity of di-PEG20K-G-CSF and mono-PEG20K-G-CSF was measured to compare the change in the activity with the number of PEG molecules attached (FIG. 7).

CPE assay was performed as follows.

$2.5 \times 10^6$ cells ($5 \times 10^5$ cells/ml) of M-NFS-60 were subcultured on 60 mm dishes. Each of native G-CSF (control), mono-mPEG20000-G-CSF, and di-mPEG20000-G-CSF was diluted to the concentration of 1 ng/µl and added to 96 well plates containing $1 \times 10^4$ cells in each well, followed by serial dilution. The dishes were incubated at 37° C. for 2 days. Then each well was then treated with 50 µl of XTT kit (Roche, Germany). Plates were incubated for another 4 hours at 37° C. and O.D. value of the plate was read at 490 nm using ELISA reader.

TABLE 1

| Cell Proliferation Assay (Measurement of activity) | |
| --- | --- |
| Conjugates | Activity (compared to native G-CSF, %) |
| Native G-CSF | 100 (FIG. 3) |
| mPEG5000-NHS-G-CSF(lysine)(Example 13) | 55 ± 5 (FIG. 3) |
| mPEG10000-NHS-G-CSF(lysine)(Example 14) | 50 ± 10 (FIG. 3) |
| Mono-mPEG20000-NHS-G-CSF(lysine)(Example 15) | 40 ± 10 (FIG. 7) |
| di-mPEG20000-NHS-G-CSF(lysine)(Example 15) | 20 ± 10 (FIG. 7) |
| mPEG(5000)-maleimide-G-CSF(thiol)(Example 9) | 50 ± 5 (FIG. 4) |
| mPEG(20000)-maleimide-G-CSF(thiol)(Example 10) | 35 ± 5 (FIG. 4) |

Table 1 shows that the biological activity varies with molecular weight of PEG molecules as well as the number of PEG molecules attached to G-CSF. di-PEG-G-CSF shows low activity compared to mono-PEG-G-CSF. Also PEG-G-CSF with thiol group modification shows a similar activity as PEG-G-CSF with amine group modification.

Also, as shown in FIG. 7, mono-PEG20K-G-CSF represents one PEG molecule attached to one G-CSF by covalent bonding, and di-PEG20K-G-CSF means two or more PEGs attached to one of G-CSF molecule. Di-PEG20K-G-CSF appeared to retain approximately 50% of biological activity of mono-PEG20K-G-CSF. Therefore, it is confirmed that 1:1 conjugates of PEG and G-CSF had higher biological activity than 2 or more:1 conjugates of PEG and G-CSF, and that when the same number of PEG were conjugated to G-CSF through thiol groups of cysteine residues or amine groups of G-CSF, there was no significant difference in the biological activity between them.

These results show that the activity decreases with the increased molecular weight of PEG molecules, and 1:1 conjugates of PEG and G-CSF retain better activity than PEG-G-CSF conjugates with two or more PEGs attached.

5. Determination of Stability of PEG-G-CSF

EXAMPLE 18

Stability of PEG-G-CSF

The stability of mPEG(5000)-maleimde-G-CSF, mPEG(20000)-maleimide-G-CSF and mPEG(10000)-NHS-G-CSF prepared in <Example 9>, <Example 10> and <Example 14>, respectively was determined by HPLC and SDS-PAGE to detect the dePEGylation of PEG molecules from PEG-G-CSF conjugates (FIG. 5).

Figure 8:
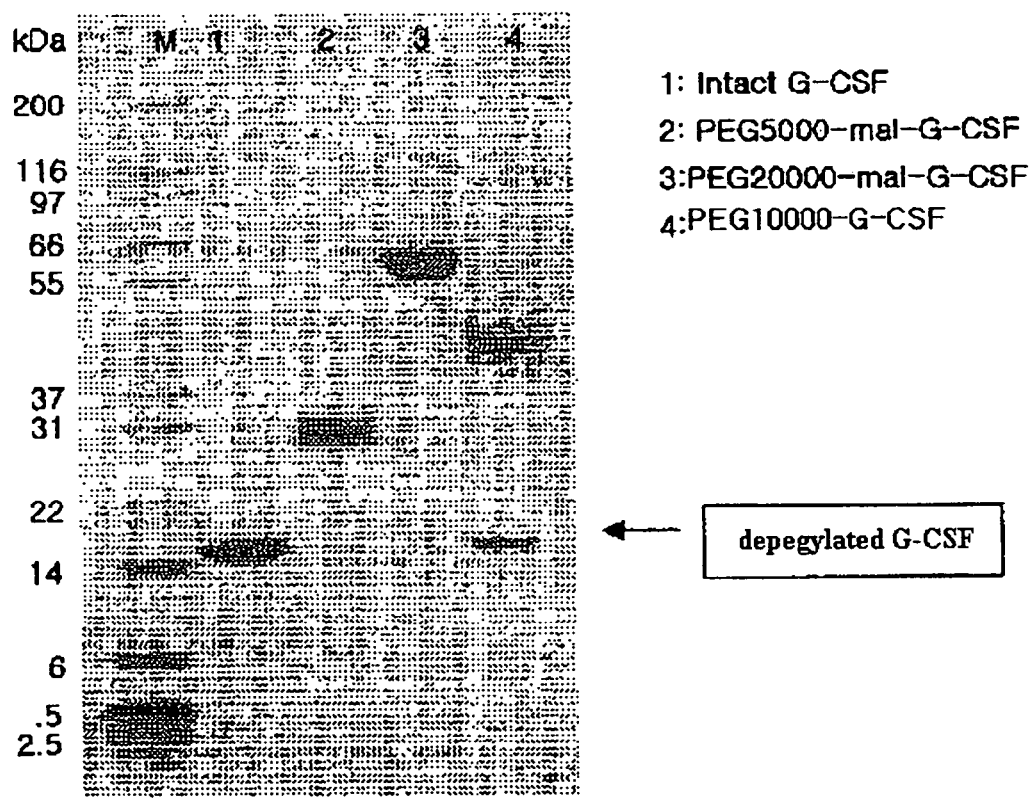
FIG. 8 shows SDS-PAGE result of mPEG5000-maleimide-G-CSF, mPEG20000-maleimide-G-CSF and mPEG10000-G-CSF. 1: native G-CSF, 2: mPEG5000-maleimide-G-CSF, 3: mPEG20000-maleimide-G-CSF, 4: mPEG10000-G-CSF

PEG-G-CSF samples in 0.1 M sodium phosphate buffer solution, pH 7.0 were stored at 4° C. for 2 weeks and the stability was determined by size exclusion HPLC using Zorbax column (Agilenet, USA) using UV detector at 220 nm to detect the amount of native G-CSF which was detached from PEG-G-CSF conjugates. Also, it was confirmed that PEG had been detached from PEG10000-G-CSF by SDS-PAGE (FIG. 8).

As a result, mPEG(10000)-NHS-G-CSF formed by amine group modification shows 14% of dePEGylation whereas dePEGylation from mPEG(5000)-maleimide-G-CSF and mPEG(20000)-maleimide-G-CSF formed by thiol group modification was not detected, indicating that mPEG-maleimide-G-CSF is more stable than mPEG-NES-G-CSF. Therefore, it was expected that thiol group modified G-CSF will be remained more stable than amine group modified G-CSF when administrated into the body.

As mentioned in the above Examples, the present inventors confirmed that when PEG-G-CSF is prepared through amine group modification of G-CSF according to the conventional method, the number of PEGs attached to G-CSF depends on the molar ratio of PEG molecules used, whereas according to the present invention, only one PEG is bonded covalently to G-CSF through thiol group modification of cysteine of G-CSF although a 20 to 50 fold molar excess of PEG is used, relative to G-CSF. As a result, the present method has an advantage that 1:1 conjugates of PEG and G-CSF of the present invention do not require further purification steps to obtain homogenous PEG-G-CSF.

In addition, the present inventors confirmed that the biological activity of PEG-G-CSF decreases as the molecular weight of PEG molecules which are attached to G-CSF increases, and 1:1 conjugates of PEG and G-CSF retain better biological activity than PEG-G-CSF with two or more PEGs attached (for example, di- or tri-PEG-G-CSF etc.).

It was also confirmed that PEG-G-CSF prepared according to the present invention is more stable than conventional PEG-G-CSF prepared through amine group modification, since the PEG-G-CSF of the present invention do not dePEGylated in the course of time, in contrast with amine group modified PEG-G-CSF.

The present inventors also found that almost all PEG-G-CSF conjugates prepared according to the present invention is able to remain in monomeric form when they are prepared in the presence of a small amount of SDS solution. It is suggested that SDS solution may prevent PEG-G-CSF from forming aggregates.

INDUSTRIAL APPLICABILITY

The present invention provides the 1:1 conjugates of biocompatible polymer and G-CSF bonded through a thiol group of a cysteine residue in G-CSF. Conjugates of biocompatible polymer-G-CSF of the present invention have improved stability and biological activity.

What is claimed is:

1. A conjugate of a biocompatible polymer and wild type G-CSF, wherein the activated biocompatible polymer is bonded to wild type G-CSF at a 1:1 molar ratio through a thiol group of a cysteine residue free of disulfide bonds corresponding to the position 17 (C17) of the mature human wild-type G-CSF.

2. The conjugate according to claim 1, wherein the biocompatible polymer is selected from the group consisting of polyethylene glycol (PEG) and derivatives thereof, polypropylene glycol (PPG), polyoxyethylene (POE), polytrimethylene glycol, polylactic acid and derivatives thereof, polyacrylic acid and derivatives thereof, polyamino acid, poly(vinyl alcohol), polyurethane, polyphosphazene, poly(L-lysine), polyalkylene oxide (PAO), polysaccharide, dextran, polyvinyl pyrrolidone, polyvinyl alcohol (PVA), polyacryl amide and similar non-immunogenic polymers.

3. The conjugate according to claim 1, wherein the wild type G-CSF originates and is purified from a natural or recombinant protein source.

4. The conjugate according to claim 1, wherein the reactive functional group in the biocompatible polymer for activation is selected from the group consisting of maleimide, acetamide, pentenoic amide, butenoic amide, isocyanate, isothiocyanate, cyanuric chloride, 1,4-benzoquinone, and disulfide.

5. The conjugate according to claim 1, wherein the biocompatible polymer is selected from the group consisting of polyethylene glycol (PEG) and derivatives thereof.

6. The conjugate according to claim 1, wherein the biocompatible polymer is selected from the group consisting of polyethylene glycol (PEG)s.

7. The conjugate according to claim 1, wherein the reactive functional group in the biocompatible polymer for activation is maleimide.

8. The conjugate according to claim 1, wherein the reactive functional group in the biocompatible polymer for activation is disulfide.

9. The conjugate according to claim 1, wherein the biocompatible polymer has a molecular weight of between 2,000 and 40,000 Daltons.

10. A conjugate of a biocompatible polymer and wild type G-CSF that has a methionine residue at position 1, wherein the activated biocompatible polymer is bonded to wild type G-CSF at a 1:1 molar ratio through a thiol group of a cysteine residue free of disulfide bonds corresponding to the position 17 (C17) of the mature human wild-type G-CSF.

\* \* \* \* \*